Aug. 30, 1938. J. N. MEADOWCROFT Plant Pat. 289
ROSE PLANT
Filed Dec. 30, 1937
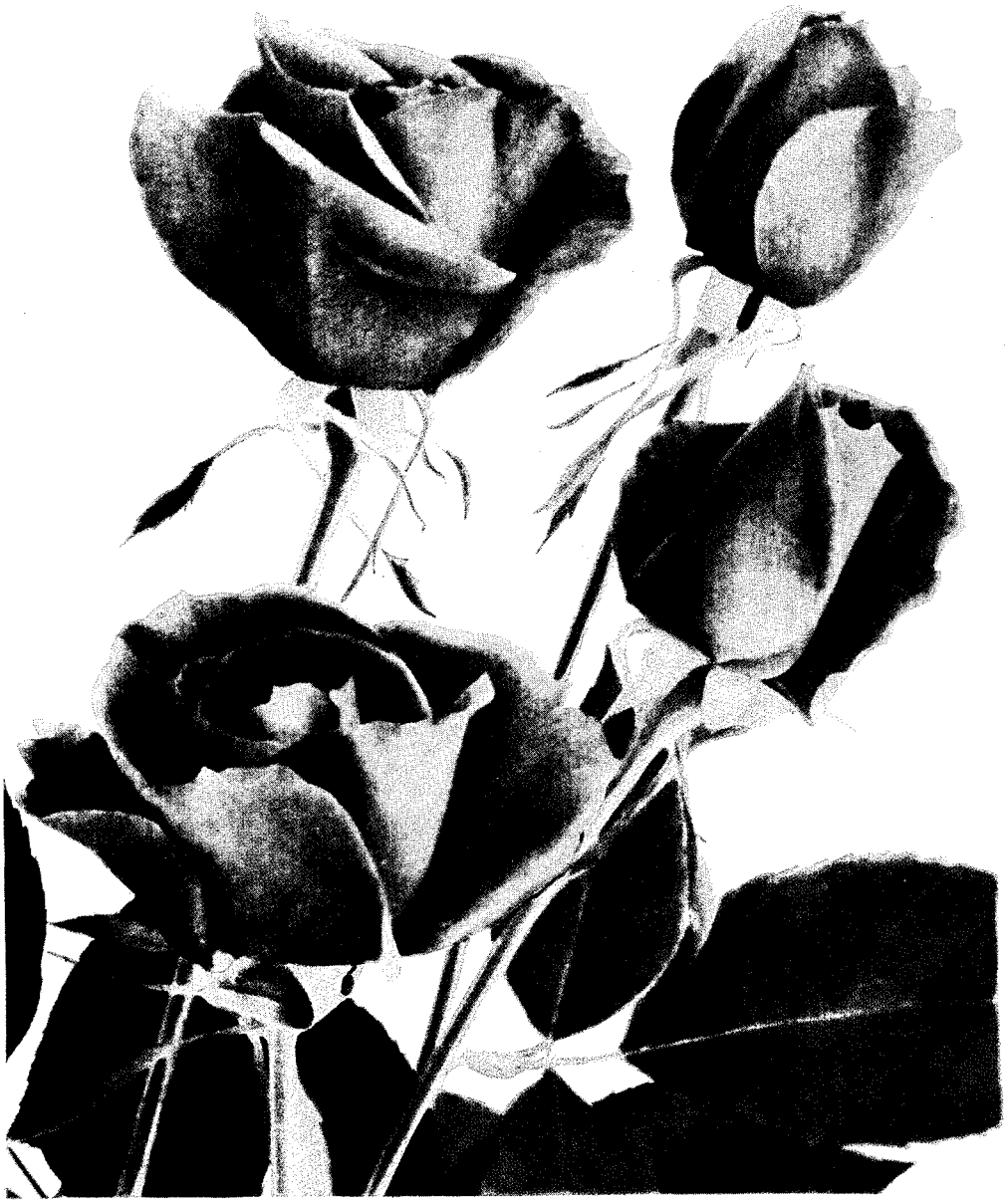
INVENTOR
James N. Meadowcroft
By Orville M. Kile
Plant Patent Agent Patented Aug. 30, 1938

Plant Pat. 289

UNITED STATES PATENT OFFICE

289

ROSE PLANT

James N. Meadowcroft, Kennett Square, Pa., assignor to J. H. Thompson's Sons, Kennett Square, Pa.

Application December 30, 1937, Serial No. 182,622

1 Claim. (Cl. 47—61)

My present invention relates to roses of the hybrid tea class and is the result of definite breeding efforts to obtain a superior red rose. The particularly desirable qualities obtained are the brilliance of color and the velvety appearance. The first cross was made in 1925 between Butterfly and a dark sport of Columbia. The lineage of this rose is traced as follows: Butterfly x a dark sport of Columbia x Red Premier x a sport of E. G. Hill x a dark sport of Briarcliff. The resulting seedling has been asexually reproduced through several generations and its qualities have proven to be firmly established.

The accompanying illustrations show four specimens of this rose in varying stages of opening. The color and aspect is shown to the best of the artist's ability, but it must be understood that the flower itself has much more brilliance of color and a more velvety aspect than is shown.

A more complete description of this variety follows. Color plate references are to Ridgway's Color Standards and Nomenclature.

*The plant*

*Growth habit.*—Vigorous, upright bush of medium height. Very strong grower and exceedingly prolific.

*Blooming habit.*—Continuous and free bloomer. Flower is borne singly on long stems.

*Foliage.*—Very abundant. The first leaf below peduncle is usually lobed, sometimes compound. Other leaves compound, having five to seven leaflets.

*Leaflets.*—Oval, with sharp-pointed apex.

*Color.*—Dark Dull Yellow-Green (Plate XXXII) on upper surface. Light Hellebore Green (Plate XVII) on under surface.

*Rachis.*—Upper side grooved and bronze. Under side green; smooth except for two or three very sharp thorns.

*Stipules.*—Clinging; moderate width. Long, straight points.

*Sepals.*—Medium in length, slightly foliaceous.

*Stems.*—Stiff. Beset with many large, sharp thorns. Calla Green (Plate V) but bronzed on side next sun.

*Thorns.*—Large. Sharp. Downward pointing. Whitish green or pink.

*Peduncle.*—Medium length. Stiff, erect, bronzy, smooth.

*The flower*

*Bud.*—Opens evenly.

*Form.*—Long and slender.

*Size.*—One and one-half to two inches long in the cutting stage.

*Color.*—Pomegranate Purple (Plate XII).

*Blossom*—

*Form.*—Imbricated. Inner petals usually twisted and intertwined.

*Size.*—Medium, having a spread of 3½ to 4 inches.

*Petalage.*—About 33 in the month of November in Pennsylvania.

*Petals.*—Of heavy substance; velvety. Outer petals almost globular in shape with slight point at apex. Drop off cleanly.

*Color.*—Under side of petals is Pomegranate Purple (Plate XII). Upper surface is nearest to Carmine (Plate I) of any color shown in Ridgway's Color Standards and Nomenclature, but with an added brilliance of color and a velvety appearance. In the sunlight, the blossom has the appearance of velvet of the color of Spectrum Red (Plate I). The color is evenly distributed over the petal except for a small yellow aiglet and an occasional white streak down the middle of some of the petals, either on the upper or lower surface.

*Keeping qualities.*—Excellent.

*Fragrance.*—Moderate.

*Reproductive organs*

*Stamens.*—Many. Uneven lengths.

*Anthers.*—Large. Yellow.

*Pistils.*—Many.

*Styles.*—Of reddish tint.

*Stigmas.*—Greenish-white.

*Ovary.*—Largely enclosed.

*Hips.*—Small and tapered.

*Comparisons*

The variety of rose known to me which is most like my new rose is the variety Better Times, but they differ in many points, the most important of which are as follows:

1. My new variety is a darker red color, is more velvety and much more brilliant.

2. My new variety produces a great many more blooms and is a much stronger grower.

3. My new variety has many more thorns on the stems.

4. The foliage of my new variety is larger and has a greater proportion of leaves with seven leaflets.

Having thus disclosed my invention, I claim:

The new and distinct variety of hybrid tea rose plant as shown and described, characterized particularly by its strong and prolific growth, and its blossoms of distinctive brilliant color and velvety aspect.

JAMES N. MEADOWCROFT.